United States Patent
Hsu et al.

(10) Patent No.: US 11,512,123 B2
(45) Date of Patent: Nov. 29, 2022

(54) METHOD FOR REMOVING WATER FROM COMPOUND SOLUTION AND PERFORMING CONJUGATE ACID CONVERSION

(71) Applicant: CHUNGHWA CHEMICAL SYNTHESIS & BIOTECH CO. LTD., New Taipei (TW)

(72) Inventors: Yao-Lung Hsu, New Taipei (TW); Kuang-Chan Hsieh, New Taipei (TW); Hui-Wen Cheng, New Taipei (TW); Zong-Han Yang, New Taipei (TW)

(73) Assignee: CHUNGHWA CHEMICAL SYNTHESIS & BIOTECH CO. LTD., New Taipei (TW)

( * ) Notice: Subject to any disclaimer, the term of this patent is extended or adjusted under 35 U.S.C. 154(b) by 18 days.

(21) Appl. No.: 17/184,164

(22) Filed: Feb. 24, 2021

(65) Prior Publication Data

US 2021/0347844 A1 Nov. 11, 2021

(30) Foreign Application Priority Data

May 11, 2020 (TW) ................... 109115553

(51) Int. Cl.
*C07K 14/635* (2006.01)
*C07K 1/34* (2006.01)
*C07K 7/06* (2006.01)

(52) U.S. Cl.
CPC .............. *C07K 14/635* (2013.01); *C07K 1/34* (2013.01); *C07K 7/06* (2013.01)

(58) Field of Classification Search
None
See application file for complete search history.

(56) References Cited

U.S. PATENT DOCUMENTS

2004/0097714 A1* 5/2004 Maubois ................ A61P 37/02
530/399

* cited by examiner

*Primary Examiner* — Sergio Coffa
(74) *Attorney, Agent, or Firm* — Muncy Geissler Olds & Lowe P.C.

(57) ABSTRACT

The present invention relates to a method for removing water from a compound solution and performing conjugate acid conversion. The method uses a nanometer film to perform reverse osmosis for the compound solution to remove water, and provides a conjugate acid to replace the acidic substances in the compound solution in order to obtain compound conjugate acid salts. The method of the present invention can effectively reduce the water content of the compound solution and replace the conjugate acid of the compound to form the desired compound conjugate acid salt.

8 Claims, 1 Drawing Sheet

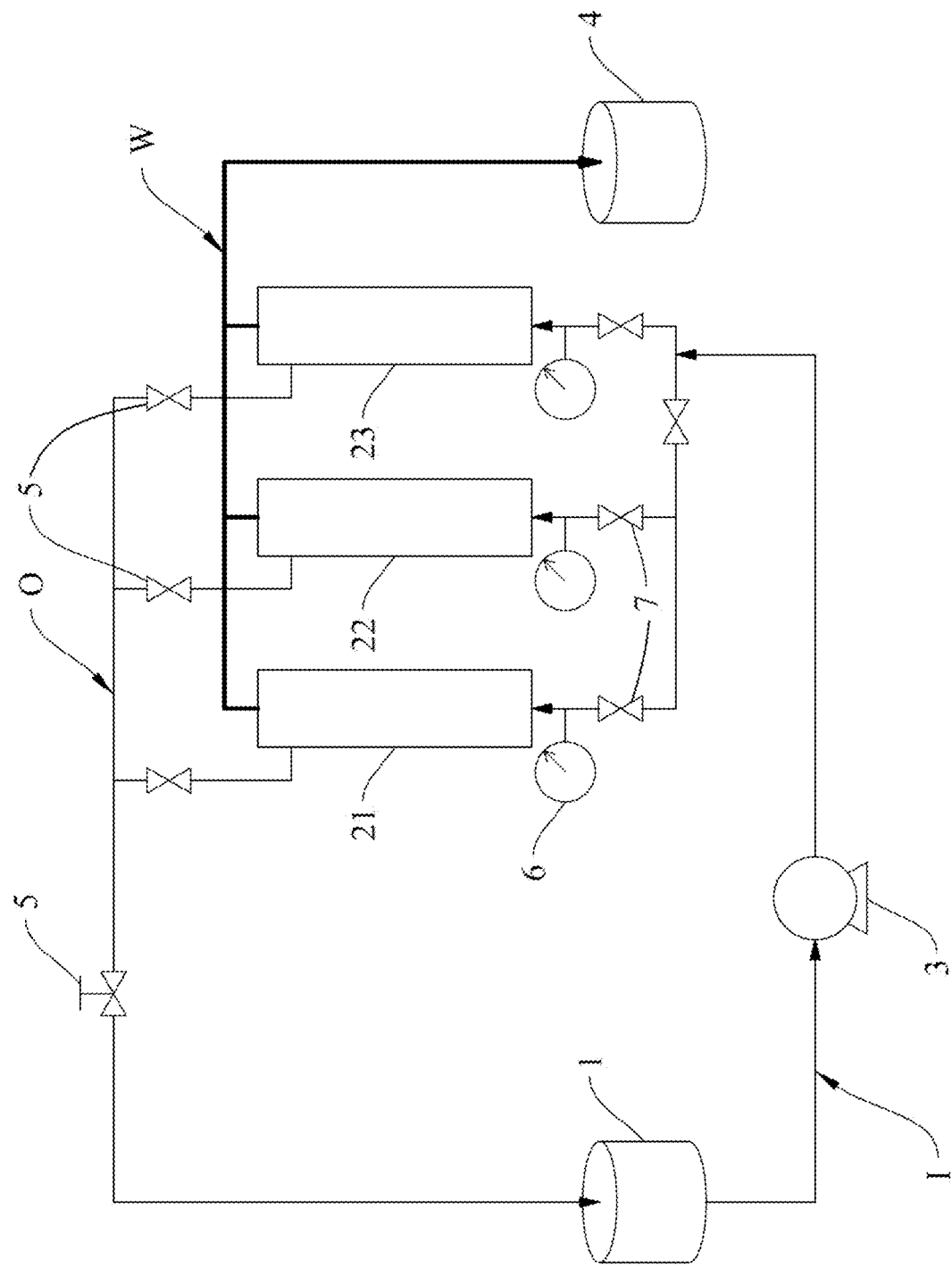

METHOD FOR REMOVING WATER FROM COMPOUND SOLUTION AND PERFORMING CONJUGATE ACID CONVERSION

BACKGROUND OF THE INVENTION

1. Technical Field

The present invention relates to a method for removing water from a compound solution and performing conjugate acid conversion, in particular using a nanometer film for reverse osmosis removal of water and performing conjugate acid substitution of the compound, and the compound is particularly a peptide compound.

2. Description of Related Art

Peptides and proteins are compounds formed by the condensation reaction of different amino acids. There are many types of peptides and proteins and they play a very important role in the organism. In addition to fermentation, the methods for preparing peptides and proteins include solid phase chemical synthesis and liquid phase chemical synthesis. In solid phase chemical synthesis and liquid phase chemical synthesis, acidic substances are usually used to remove protective groups or solid supports. The most commonly used acidic substance is trifluoroacetic acid, so trifluoroacetic acid is the most common residual substance.

In order to modify and optimize the properties of a compound, the compound is usually reacted with a conjugate acid (i.e., a counter ion) to form a compound salt so as to change its solubility, dissolution rate, stability, and crystal habits. Trifluoroacetic acid is not a common conjugate acid that can be used to form compound salts. Therefore, it is necessary to reduce the trifluoroacetic acid content of synthesized peptides or proteins and replace trifluoroacetic acid with a conjugate acid with dosage stability or high bioavailability. At present, there are two methods to remove trifluoroacetic acid from peptides and proteins. First, column chromatography allows peptides or proteins to stay on the stationary phase material in the column, and an acidic solution other than trifluoroacetic acid (i.e., a compound conjugate acid) is used as the eluent for replacement. Second, to let the peptide or protein solution flow through an ion exchange resin, and the cations contained on the surface of the resin can retain trifluoroacetic acid. In operation, the ion exchange resin is washed with strong base and then washed with the required conjugate acid, and then the peptide or protein is allowed to flow into the resin, and the peptide or protein solution containing less trifluoroacetic acid is collected after elution. However, unlike chromatographic separation, ion exchange resin cannot provide an effective chromatographic purification process and can only be used for replacement by the conjugate acid on the resin.

BRIEF SUMMARY OF THE INVENTION

If the water in the synthesized peptide or protein aqueous solution can be effectively reduced and the organic solvent and trifluoroacetic acid can be removed, the downstream purification process can be more flexible and improve efficiency. The reason is that chromatographic purification is carried out in the downstream purification process, which usually produces more aqueous solutions, and peptides or proteins are easily soluble in high water phase. It usually takes a long time to remove water and organic solvents with a vacuum concentrator. If lyophilization is used, the organic solvent in the aqueous solution will affect the freezing efficiency and even damage the pump. Therefore, the chromatographic purification process of peptides or proteins has the problems of multiple steps, cumbersome process, long operation time and high production cost.

Therefore, the present invention intends to provide a peptide or protein solution that facilitates the downstream purification process more efficiently. The objective of the invention is to provide a method for removing water from a compound solution and performing conjugate acid conversion in the same environment, which can effectively remove water and trifluoroacetic acid from the peptide or protein aqueous solution.

That is, the method for removing water from a compound solution and performing conjugate acid conversion of the present invention includes the steps of: (a) removing water: providing a compound solution containing an acidic substance A, pressurizing the compound solution to penetrate at least one nanometer film for reverse osmosis, and then discharging the aqueous solution obtained by reverse osmosis; (b) providing conjugate acid: providing an acidic substance B aqueous solution different from the acidic substance A to the nanometer film; (c) acid conversion and water removal: pressurizing for reverse osmosis, and discharging the aqueous solution obtained by reverse osmosis, acidic substance A and excess acidic substance B; (d) cleaning: adding water, pressurizing for reverse osmosis, and then discharging the aqueous solution obtained by reverse osmosis and excess acidic substance B; and (e) collection: adding water to clean the compound concentrate.

In a preferred embodiment, the acidic substance A is trifluoroacetic acid.

In a preferred embodiment, the acidic substance B is hydrochloric acid, hydrofluoric acid, sulfuric acid, acetic acid, benzoic acid, benzenesulfonic acid, bromic acid, hypobromous acid, camphorsulfonic acid, chloride, citric acid, methanesulfonic acid, fumaric acid, glucoheptonic acid, sodium glucoheptonate, hippuric acid, iodide, isethionic acid, lactic acid, lactobionic acid, sodium laureth sulfate, malic acid, maleic acid, mesylate, methanesulfonic acid, naphthoic acid, naphthalenesulfonic acid, nitric acid, stearic acid, oleic acid, sodium oleate, oxalic acid, palmitic acid, phosphoric acid, polygalacturonic acid, succinic acid, sulfuric acid, sulfosalicylic acid, tartaric acid, or p-toluenesulfonyl.

In a preferred embodiment, any one or more of the steps (a) to (d) are repeated at least twice.

In a preferred embodiment, the compound is a protein or peptide.

In a preferred embodiment, the peptide comprises etetcalcetide, teriparatide, or abaloparatide.

In a preferred embodiment, the nanometer film includes a nanofiltration membrane or a reverse osmosis membrane.

In a preferred embodiment, the material of the nanometer film includes cellulose acetate fiber, polysulfone, polyvinylidene fluoride, polyethersulfone resin, or a composite film of a combination thereof.

In a preferred embodiment, the step (e) is further followed by a step (f) lyophilization: freeze drying the compound concentrate containing the acidic substance B to obtain a salt of the compound.

In a preferred embodiment, a cleaning step is further performed between the step (a) and the step (b): washing the nanometer film with water and then discharging the washed aqueous solution.

Compared with the conventional technology, the present invention provides a method for removing water from a compound solution and performing conjugate acid conversion in the same environment, which can effectively remove water and acidic substances (especially trifluoroacetic acid) from the peptide or protein aqueous solution. The method can facilitate the purification of downstream peptides or proteins and improve the efficiency of the downstream purification process.

BRIEF DESCRIPTION OF THE FIGURE

The FIGURE shows an apparatus using the method of the present invention for removing water from a compound solution and performing conjugate acid conversion.

DETAILED DESCRIPTION OF THE INVENTION

The following embodiments should not be regarded as excessively limiting the present invention. The persons with ordinary knowledge in the technical field of the present invention can modify and change the embodiments discussed herein without departing from the spirit or scope of the invention, and the modification and variation still fall within the scope of the invention.

The method for removing water from a compound solution and performing conjugate acid conversion of the present invention includes the steps of: (a) removing water: providing a compound solution containing an acidic substance A, pressurizing the compound solution to penetrate at least one nanometer film for reverse osmosis, and then discharging the aqueous solution obtained by reverse osmosis; (b) providing conjugate acid: providing an acidic substance B aqueous solution different from the acidic substance A to the nanometer film; (c) acid conversion and water removal: pressurizing for reverse osmosis, and discharging the aqueous solution obtained by reverse osmosis, acidic substance A and excess acidic substance B; (d) cleaning: adding water, pressurizing for reverse osmosis, and then discharging the aqueous solution obtained by reverse osmosis and excess acidic substance B; and (e) collection: adding water to elute the compound concentrate.

Furthermore, the step (e) may be followed by a step (f) lyophilization: freeze drying the compound concentrate containing the acidic substance B to obtain a salt of the compound.

Furthermore, a cleaning step is further performed between the step (a) and the step (b): washing the nanometer film with water and then discharging the washed aqueous solution. Any one or more of the steps (a) to (d) are repeated at least twice.

The nanometer film filtration device shown in the FIGURE uses the method of the present invention for removing water from a compound solution and performing conjugate acid conversion. The nanometer film filtration device includes a solution storage tank 1, nanometer film filter elements 21.22.23, a peristaltic pump 3, a waste liquid tank 4, a water outlet valve 5, a pressure indicator 6, and a water inlet valve 7. The nanometer film filter elements 21.22.23 contain nanometer films. The specific operation process of the nanometer film filtration device is as follows: A compound solution containing an acidic substance A is put into the solution storage tank 1 and transported to the nanometer film filter elements 21.22.23 via the peristaltic pump 3 (transportation path I). Reverse osmosis of the compound solution containing the acidic substance A is performed by the nanometer films in the nanometer film filter elements 21.22.23, i.e., the compound containing the acidic substance A is dewatered. The aqueous solution obtained by reverse osmosis will be discharged from the nanometer film filter elements 21.22.23 and transported to the waste liquid tank 4 (transportation path W). The aqueous solution that has not been permeated by reverse osmosis will be transported to the solution storage tank 1 (transportation path O), and then transported to the nanometer film filter elements 21.22.23 through the peristaltic pump 3 for the next reverse osmosis. That is, the nanometer film filtration device is a circulating filtration device, wherein the pressure control of the nanometer film filter elements 21.22.23 is accomplished by regulating the water outlet valve 5 and the water inlet valve 7, and the pressure of the nanometer film filter elements 21.22.23 will be displayed on the pressure indicator 6. In the steps (b) and (c), an aqueous solution of acidic substance B different from the acidic substance A is put into the solution storage tank 1, and is subjected to acid conversion and water removal through the transportation paths I and O, and then the aqueous solution obtained by reverse osmosis, the acidic substance A and the excess acidic substance B are discharged to the waste liquid tank 4 via the transportation path W. In the cleaning step between the step (a) and the step (b) and in the step (d), water is put into the solution storage tank 1, and the transportation paths I and O are repeatedly circulated to clean the inside of the nanometer film filter elements 21.22.23, and then the aqueous solution obtained by reverse osmosis is discharged to the waste liquid tank 4 through the transportation path W. In the step (e), water is put into the solution storage tank 1, and the compound concentrate in the nanometer film filter elements 21.22.23 is washed out through the transportation paths I and O, and then the compound concentrate will be transported back through the transportation path O and collected in the solution storage tank 1.

The pressurizing pressure in the steps (a), (c) and (d) can be adjusted by the water inlet valve 7 and the water outlet valve 5. The pressurizing pressure can be 50-100 psi, preferably 60-90 psi, and more preferably 70-80 psi. This pressure range can effectively remove the water in the peptide or protein solution and facilitate the removal of water. When the pressure is lower than 50 psi, the solution will not be able to pass through the nanometer film, and when the pressure is higher than 100 psi, the pump will not be able to withstand the pressure.

The compound is a protein or peptide, and the present invention is not limited to these.

The peptides include etetcalcetide, teriparatide or abaloparatide, and the present invention is not limited to these.

The acidic substance A is trifluoroacetic acid, and the present invention is not limited to it.

The method of preparing the compound solution containing the acidic substance A is as follows: The compound is dissolved in the solution containing the acidic substance A so that each 1 liter of the solution containing the acidic substance A contains at most 20 g of the compound. When the concentration of the compound exceeds 20 g/L, the concentration is too high, which will cause blockage of the nanometer film, increase in the pressure of the inner tubes of the nanometer film filter elements 21.22.23, and damage to the pump. The solution containing the acidic substance A may contain water, an organic solvent and the acidic substance A, wherein the content of water is 0-100% (v/v), the content of the organic solvent is up to 20% (v/v), and the content of the acidic substance A is up to 50% (v/v). If the content of the organic solvent exceeds 20% (v/v), the nanometer film will be damaged and its filtering function will be lost. If the content of the acidic substance A exceeds 50% (v/v), the compound will be deteriorated and the stainless steel of the nanometer film filter element will be corroded.

The organic solvent may be a protic solvent, such as methanol or ethanol, of which methanol is preferred.

The acidic substance B is the conjugate acid of the acidic substance A, which is used to replace the acidic substance A in the compound solution, i.e., the acidic substance A is converted into the acidic substance B. The acidic substance B includes, but is not limited to, hydrochloric acid, hydrofluoric acid, sulfuric acid, acetic acid, benzoic acid, benzenesulfonic acid, bromic acid, hypobromous acid, camphorsulfonic acid, chloride, citric acid, methanesulfonic acid, fumaric acid, glucoheptonic acid, sodium glucoheptonate, hippuric acid, iodide, isethionic acid, lactic acid, lactobionic acid, sodium laureth sulfate, malic acid, maleic acid, mesylate, methanesulfonic acid, naphthoic acid, naphthalenesulfonic acid, nitric acid, stearic acid, oleic acid, sodium oleate, oxalic acid, palmitic acid, phosphoric acid, polygalacturonic acid, succinic acid, sulfuric acid, sulfosalicylic acid, tartaric acid, or p-toluenesulfonyl, of which hydrochloric acid and acetic acid are preferred.

The method of the present invention utilizes the acidic substance B to replace the acidic substance A, and to form the desired compound conjugate acid salt with the compound. Therefore, the "excess acidic substance B" refers to the acidic substance B that has not replaced the acidic substance A, i.e., the excessive acidic substance B. In the step (c), part of the excess acidic substance B is discharged first, and then in the step (d), the excess acidic substance B is discharged again by washing to reduce the acidic substance B in the compound concentrate.

The volume concentration (v/v) of the acidic substance B aqueous solution is 0.01-50%, preferably 0.05-30%, and more preferably 0.10-10%, for example 0.01%, 0.05%, 0.10%, 0.15%, 0.20%, 0.25%, 0.5%, 0.75%, 1.5%, 2%, 2.5%, 3%, 4%, 5%, 10%, 15%, 20%, 25%, 30%, 35%, 40%, 45% or 50%, and the present invention is not limited thereto. If the volume concentration of the acidic substance B exceeds 50% (v/v), the peptide or protein solution sample will become unstable or deteriorate.

The nanometer film includes, but is not limited to, nanofiltration membrane or reverse osmosis membrane. Its brand name is, for example, GE, and its model number is, for example, CK, Duracid, DK, DL, HL, AD, AE, AG, AK, SC, SE, CD, CE, CG, or Duraslick RO. The material of the nanometer film includes, but is not limited to, cellulose acetate fiber, polysulfone, polyvinylidene fluoride, polyethersulfone resin, or a composite film of a combination thereof. The nanometer film can be passed through by substances with molecular weight less than 500 Da, preferably 300 Da, and more preferably 150 Da.

Embodiment

The details and technical solution of the present invention are hereunder described with reference to accompanying drawing. For illustrative sake, the accompanying drawing is not drawn to scale. The accompanying drawing and the scale thereof are not restrictive of the present invention.

Embodiments 1 to 9 used the nanometer film filtration device shown in the FIGURE to implement the method of the present invention.

In Embodiments 1 to 9, "TFA residue %", "AcOH content %" and "HCl content %" respectively refer to the weight percentage (%) of trifluoroacetic acid (TFA), acetic acid (AcOH) and hydrochloric acid (HCl) in the sample.

Preparation Example

A solution containing 89.9% (v/v) of water, 10% (v/v) of methanol and 0.1% (v/v) of trifluoroacetic acid was prepared for dissolving peptide or protein, i.e., the solution containing the acidic substance A of the present invention.

Embodiment 1

In this embodiment, the compound was etetcalcetide, and the acidic substance A was trifluoroacetic acid (TFA), and the acidic substance B was hydrochloric acid (HCl).

4 g of etetcalcetide was dissolved in the solution of the preparation example and the solution was quantified to 7.5 L to obtain an etetcalcetide solution. Then the etetcalcetide solution was poured into the solution storage tank 1, and the injection tube and the retention tube were put into the solution storage tank 1. The peristaltic pump 3, the water inlet valve 7 and the water outlet valve 5 were turned on to deliver the etetcalcetide solution to the nanometer film filter elements 21.22.23 for circulating water removal, wherein the flow rates of the nanometer film filter elements 21.22.23 were similar. The water outlet valve 5 was adjusted to control the pressure at about 70-80 psi. After the etetcalcetide solution in the solution storage tank 1 had entered the nanometer film filter elements 21.22.23, the etetcalcetide solution was poured into the solution storage tank 1 again, and then the peristaltic pump 3 was turned on and the water outlet valve 5 was adjusted to remove water, and this process was repeated 3 times.

After that, the nanometer film filter elements 22 and 23 were turned off, and 400 mL of water was added to the solution storage tank 1 and circulated for 1 minute to dissolve and collect the etetcalcetide on the nanometer film of the nanometer film filter element 21, and this process was repeated 3 times. The nanometer film filter element 21 was turned off, the nanometer film filter elements 22 and 23 were turned on, the collected etetcalcetide solution was put into the solution storage tank 1, and then the peristaltic pump 3 was turned on and the water outlet valve 5 was adjusted to remove water. The nanometer film filter element 23 was turned off, 400 mL of water was added and circulated for 1 minute to dissolve and collect the etetcalcetide on the nanometer film, and this process was repeated 3 times. The nanometer film filter elements 21 and 22 were turned off, the nanometer film filter element 23 was turned on, the collected etetcalcetide solution was put into the solution storage tank 1, and then the peristaltic pump 3 was turned on and the water outlet valve 5 was adjusted to remove water.

Finally, 0.10% (v/v) hydrochloric acid aqueous solution (HCl/H$_2$O) was used as the acidic substance B aqueous solution and added to the solution storage tank 1, the nanometer film filter element 23 and the peristaltic pump 3 were turned on and circulated for 1 minute, and then the water outlet valve 5 was turned on and adjusted to remove water, and this process was repeated 12 times. Water was put into the solution storage tank 1, the nanometer film filter element 23 and the peristaltic pump 3 were turned on and circulated for 1 minute, and then the water outlet valve 5 was turned on and adjusted to remove water, and this process was repeated 3 times. The etetcalcetide solution in the nanometer film filter element 23 was collected, the etetcalcetide on the nanometer film was eluted with 400 mL of water and collected, and this process was repeated 3 times.

Embodiment 2

The test procedure of this embodiment was the same as that of Embodiment 1. The only difference was that 0.50% (v/v) hydrochloric acid aqueous solution (HCl/H$_2$O) was used as the acidic substance B aqueous solution.

Embodiment 3

The test procedure of this embodiment was the same as that of Embodiment 1. The only difference was that 2.50% (v/v) hydrochloric acid aqueous solution (HCl/H$_2$O) was used as the acidic substance B aqueous solution.

The test results of Embodiments 1 to 3 are shown in Table 1: The etetcalcetide solutions of Embodiments 1 to 3 were all 7.5 L before water removal and 0.4 L after water removal. The water removal rate reached 94.67%. In order to monitor the changes in the residual amount of trifluoroacetic acid (TFA) and the content of hydrochloric acid, the sample aqueous solutions obtained after repeated addition of the hydrochloric acid aqueous solution 12 times and circulating water removal were sequentially collected and detected, and then the $0^{th}$, $3^{rd}$, $6^{th}$, $9^{th}$ and $12^{th}$ sample aqueous solutions were analyzed. The results show that the TFA residue % of Embodiments 1 to 3 would decrease as the number of additions of hydrochloric acid aqueous solution (HCl/H$_2$O) increased, i.e., when the addition of hydrochloric acid increased, the TFA residue % would decrease accordingly. In addition, compared with Embodiments 1 and 2, in Embodiment 3, no TFA was detected at the 6, 9 and 12 times, and the TFA residue % reached below the detection limit (ND). Obviously, when the concentration of hydrochloric acid was higher, the residual amount of TFA decreased. The higher the concentration of hydrochloric acid aqueous solution (HCl/H$_2$O), the higher the hydrochloric acid content, the more the hydrochloric acid content of etetcalcetide aqueous solution should be, but the hydrochloric acid content would reach saturation at about 15%. As shown in Table 1, after adding the hydrochloric acid aqueous solution 12 times, the hydrochloric acid content of Embodiments 2 and 3 had reached saturation, which were 15.65% and 16.01%, respectively. In comparison, Embodiment 1 used 0.10% hydrochloric acid aqueous solution (HCl/H$_2$O), and its hydrochloric acid content was not saturated, which was 5.78%.

Embodiment 4

The test procedure of this embodiment was the same as that of Embodiment 1. The only difference was that the compound was teriparatide and that 0.10% acetic acid aqueous solution (AcOH/H$_2$O) was used as the acidic substance B aqueous solution.

Embodiment 5

The test procedure of this embodiment was the same as that of Embodiment 1. The only difference was that the compound was teriparatide and that 0.50% acetic acid aqueous solution (AcOH/H$_2$O) was used as the acidic substance B aqueous solution.

Embodiment 6

The test procedure of this embodiment was the same as that of Embodiment 1. The only difference was that the compound was teriparatide and that 2.50% acetic acid aqueous solution (AcOH/H$_2$O) was used as the acidic substance B aqueous solution.

The test results of Embodiments 4 to 6 are shown in Table 2: The teriparatide solutions of Embodiments 4 to 6 were all 7.5 L before water removal and 0.4 L after water removal. The water removal rate reached 94.67%. In order to monitor the changes in the residual amount of trifluoroacetic acid (TFA) and the content of acetic acid aqueous solution (AcOH/H$_2$O), the sample aqueous solutions obtained after repeated addition of hydrochloric acid aqueous solution 12 times and circulating water removal were successively collected and detected, and then the $0^{th}$, $3^{rd}$, $6^{th}$, $9^{th}$ and $12^{th}$ sample aqueous solutions were analyzed. The results show that the higher the concentration of acetic acid aqueous solution (AcOH/H$_2$O), the slight decrease in the residual amount of TFA, or the more times the acetic acid aqueous solution (AcOH/H$_2$O) was added, the residual amount of TFA decreased slightly. The higher the concentration of acetic acid aqueous solution (AcOH/H$_2$O), the higher the acetic acid content, and the more acetic acid content in the teriparatide aqueous solution. However, for teriparatide aqueous solution, the acetic acid content would reach saturation at about 3%. As shown in Table 2, after the $12^{th}$ addition of hydrochloric acid aqueous solution, the acetic acid content of Embodiments 5 and 6 had reached saturation, which were 2.58% and 3.9% (i.e., close to 3%), respectively. In comparison, Embodiment 4 used 0.10% acetic acid aqueous solution (AcOH/H$_2$O), and its acetic acid content was not saturated, which was 0.79%.

TABLE 1

|  | Embodiment 1 | Embodiment 2 | Embodiment 3 |
|---|---|---|---|
| Volume before water removal | 7.5 L | 7.5 L | 7.5 L |
| Volume after water removal | 0.4 L | 0.4 L | 0.4 L |
| Water removal rate (%) | 94.67 | 94.67 | 94.67 |
| HCl/H$_2$O (v/v %) | 0.10 | 0.50 | 2.50 |

| $N^{th}$ addition | TFA residue (%) | HCl content (%) | TFA residue (%) | HCl content (%) | TFA residue (%) | HCl content (%) |
|---|---|---|---|---|---|---|
| 0 | 32.55 | ND | 30.44 | ND | 29.06 | ND |
| 3 | 25.45 | 0.11 | 1.09 | 13.02 | 0.57 | 14.55 |
| 6 | 18.46 | 1.25 | 0.2 | 14.98 | ND | 15.63 |
| 9 | 17.62 | 3.55 | 0.08 | 15.51 | ND | 15.86 |
| 12 | 15.01 | 5.78 | ND | 15.65 | ND | 16.01 |

TABLE 2

|  | Embodiment 4 | Embodiment 5 | Embodiment 6 |
|---|---|---|---|
| Volume before water removal | 7.5 L | 7.5 L | 7.5 L |
| Volume after water removal | 0.4 L | 0.4 L | 0.4 L |
| Water removal rate (%) | 94.67 | 94.67 | 94.67 |
| AcOH/H$_2$O (v/v %) | 0.10 | 0.50 | 2.50 |

| $N^{th}$ addition | TFA residue (%) | AcOH content (%) | TFA residue (%) | AcOH content (%) | TFA residue (%) | AcOH content (%) |
|---|---|---|---|---|---|---|
| 0 | 13.12 | ND | 11.62 | ND | 13.68 | ND |
| 3 | 12.85 | 0.45 | 10.01 | 1.15 | 10.51 | 1.84 |
| 6 | 9.32 | 0.9 | 8.97 | 1.9 | 8.47 | 2.37 |

TABLE 2-continued

| 9 | 4.48 | 0.98 | 7.7 | 2.7 | 6.87 | 2.85 |
| 12 | 3.58 | 0.79 | 6.98 | 2.58 | 5.15 | 3.9 |

Embodiment 7

The test procedure of this embodiment was the same as that of Embodiment 1. The only difference was that the compound was abaloparatide and that 0.10% acetic acid aqueous solution (AcOH/H$_2$O) was used as the acidic substance B aqueous solution.

Embodiment 8

The test procedure of this embodiment was the same as that of Embodiment 1. The only difference was that the compound was abaloparatide and that 0.50% acetic acid aqueous solution (AcOH/H$_2$O) was used as the acidic substance B aqueous solution.

Embodiment 9

The test procedure of this embodiment was the same as that of Embodiment 1. The only difference was that the compound was abaloparatide and that 2.50% acetic acid aqueous solution (AcOH/H$_2$O) was used as the acidic substance B aqueous solution.

The test results of Embodiments 7 to 9 are shown in Table 3: The abaloparatide solutions of Embodiments 7 to 9 were all 7.5 L before water removal and 0.4 L after water removal. The water removal rate reached 94.67%. In order to monitor the changes in the residual amount of trifluoroacetic acid (TFA) and the content of acetic acid aqueous solution (AcOH/H$_2$O), the sample aqueous solutions obtained after repeated addition of acetic acid aqueous solution (AcOH/H$_2$O) 12 times and circulating water removal were sequentially collected and detected, and then the 0$^{th}$, 3$^{rd}$, 6$^{th}$, 9$^{th}$ and 12$^{th}$ sample aqueous solutions were analyzed. The results show that the higher the concentration of acetic acid, the residual amount of TFA decreased slightly, or the more times acetic acid was added, the residual amount of TFA decreased slightly. In Embodiments 7 to 9, after adding 2.50% (v/v) acetic acid aqueous solution (AcOH/H$_2$O) for the 12$^{th}$ time, the residual amount of TFA was reduced by nearly half. For abaloparatide aqueous solution, the acetic acid content can reach saturation at about 6%. As shown in Table 3, after the 12$^{th}$ addition of hydrochloric acid aqueous solution in Embodiments 7 to 9, the acetic acid contents were 6.2%, 5.11%, and 6.27%, respectively, which were close to 6%.

TABLE 3

| | Embodiment 7 | Embodiment 8 | Embodiment 9 |
| --- | --- | --- | --- |
| Volume before water removal | 7.5 L | 7.5 L | 7.5 L |
| Volume after water removal | 0.4 L | 0.4 L | 0.4 L |
| Water removal rate (%) | 94.67 | 94.67 | 94.67 |
| AcOH/H$_2$O (v/v %) | 0.10 | 0.50 | 2.50 |

TABLE 3-continued

| N$^{th}$ addition | TFA residue (%) | AcOH content (%) | TFA residue (%) | AcOH content (%) | TFA residue (%) | AcOH content (%) |
| --- | --- | --- | --- | --- | --- | --- |
| 0 | 14.9 | ND | 11.15 | ND | 11.51 | ND |
| 3 | 13.48 | 0.1 | 11.09 | 2.16 | 10.63 | 3.1 |
| 6 | 11.00 | 2.91 | 11.26 | 2.21 | 8.74 | 5.04 |
| 9 | 7.2 | 5.75 | 9.34 | 4.37 | 6.57 | 6.21 |
| 12 | 6.89 | 6.2 | 5.99 | 5.11 | 5.76 | 6.27 |

In summary, the water removal rate of Embodiments 1 to 9 is 96.67%, i.e., the method of the present invention can effectively remove the water of the sample aqueous solution. Moreover, when the acidic substance B aqueous solution is added for the 12$^{th}$ time, the TFA residue % can reach below about 16%, i.e., the method of the invention can effectively replace the conjugate acid of the compound to form the desired compound conjugate acid salt. It is worth noting that, comparing Embodiments 1 to 3 and Embodiments 4 to 9, when the acidic substance B aqueous solution was 0.50% or more hydrochloric acid aqueous solution, the effect of replacing TFA was better. In Embodiments 2 to 3, after the 12$^{th}$ addition of hydrochloric acid aqueous solution, the TFA residue % was all without TFA detected. That is, when the method of the invention uses a relatively high concentration of hydrochloric acid aqueous solution as the acidic substance B aqueous solution, it can achieve a better TFA removal effect.

Therefore, the method of the present invention can effectively reduce the water content in the compound solution, and replace the conjugate acid of the compound to form the desired compound conjugate acid salt, so as to obtain a peptide or protein solution that is beneficial to improve the efficiency of the downstream purification process.

The above is the detailed description of the present invention. However, the above is merely the preferred embodiment of the present invention and cannot be the limitation to the implement scope of the invention, which means the variation and modification according to the present invention may still fall into the scope of the invention.

What is claimed is:

1. A method for removing water from a compound solution and performing conjugate acid conversion, comprising the steps of: (a) removing water: providing a compound solution containing an acidic substance A, pressurizing the compound solution to penetrate at least one nanometer film for reverse osmosis, and then discharging the aqueous solution obtained by reverse osmosis; (b) providing conjugate acid: providing an acidic substance B aqueous solution different from the acidic substance A to the nanometer film; (c) acid conversion and water removal: pressurizing for reverse osmosis, and discharging the aqueous solution obtained by reverse osmosis, acidic substance A and excess acidic substance B; (d) cleaning: adding water, pressurizing for reverse osmosis, and then discharging the aqueous solution obtained by reverse osmosis and excess acidic substance B; and (e) collection: adding water to elute the compound concentrate, wherein the compound is selected from etelcalcetide, teriparatide, and abaloparatide.

2. The method of claim 1, wherein the acidic substance A is trifluoroacetic acid.

3. The method of claim 1, wherein the acidic substance B is hydrochloric acid, hydrofluoric acid, sulfuric acid, acetic acid, benzoic acid, benzenesulfonic acid, bromic acid, hypobromous acid, camphorsulfonic acid, chloride, citric acid, methanesulfonic acid, fumaric acid, glucoheptonic acid, sodium glucoheptonate, hippuric acid, iodide, isethionic acid, lactic acid, lactobionic acid, sodium laureth sulfate, malic acid, maleic acid, mesylate, methanesulfonic acid, naphthoic acid, naphthalenesulfonic acid, nitric acid, stearic acid, oleic acid, sodium oleate, oxalic acid, palmitic acid, phosphoric acid, polygalacturonic acid, succinic acid, sulfuric acid, sulfosalicylic acid, tartaric acid, or p-toluenesulfonyl.

4. The method of claim 1, wherein any one or more of the steps (a) to (d) are repeated at least twice.

5. The method of claim 1, wherein the nanometer film comprises a nanofiltration membrane or a reverse osmosis membrane.

6. The method of claim 1, wherein the material of the nanometer film comprises cellulose acetate fiber, polysulfone, polyvinylidene fluoride, polyethersulfone resin, or a composite film of a combination thereof.

7. The method of claim 1, wherein the step (e) is further followed by a step (f) lyophilization: freeze drying the compound concentrate containing the acidic substance B to obtain a salt of the compound.

8. The method of claim 1, wherein a cleaning step is further performed between the step (a) and the step (b): washing the nanometer film with water and then discharging the washed aqueous solution.

* * * * *